United States Patent
Naasani

(10) Patent No.: US 7,214,428 B2
(45) Date of Patent: *May 8, 2007

(54) HIGHLY LUMINESCENT FUNCTIONALIZED SEMICONDUCTOR NANOCRYSTALS FOR BIOLOGICAL AND PHYSICAL APPLICATIONS

(75) Inventor: Imad Naasani, Columbus, OH (US)

(73) Assignee: Invitrogen Corporation, Carlsbad, CA (US)

( * ) Notice: Subject to any disclaimer, the term of this patent is extended or adjusted under 35 U.S.C. 154(b) by 390 days.

This patent is subject to a terminal disclaimer.

(21) Appl. No.: 10/410,108

(22) Filed: Apr. 9, 2003

(65) Prior Publication Data

US 2004/0009341 A1    Jan. 15, 2004

Related U.S. Application Data

(63) Continuation-in-part of application No. 10/245,082, filed on Sep. 17, 2002.

(60) Provisional application No. 60/379,208, filed on May 9, 2002, provisional application No. 60/322,982, filed on Sep. 17, 2001.

(51) Int. Cl.
*B32B 5/16* (2006.01)

(52) U.S. Cl. .................. 428/403; 428/407; 428/690; 252/301.4 R; 252/301.4 S; 252/301.6 R; 252/301.6 S

(58) Field of Classification Search ............. 428/403, 428/407, 690; 252/301.4 R, 301.4 S, 301.6 R, 252/301.6 S
See application file for complete search history.

(56) References Cited

U.S. PATENT DOCUMENTS

| | | | |
|---|---|---|---|
| 4,642,334 A | | 2/1987 | Moore et al. |
| 4,946,778 A | | 8/1990 | Ladner et al. |
| 5,034,506 A | | 7/1991 | Summerton et al. |
| 5,151,507 A | | 9/1992 | Hobbs, Jr. et al. |
| 5,187,085 A | | 2/1993 | Lee |
| 5,505,928 A | * | 4/1996 | Alivisatos et al. ......... 423/299 |
| 5,558,991 A | | 9/1996 | Trainor |
| 5,596,086 A | | 1/1997 | Matteucci et al. |
| 5,602,240 A | | 2/1997 | De Mesmaeker et al. |
| 5,637,258 A | | 6/1997 | Goldburt et al. |
| 5,679,785 A | | 10/1997 | Engels et al. |
| 5,736,137 A | | 4/1998 | Anderson et al. |
| 5,789,157 A | | 8/1998 | Jensen et al. |
| 5,948,386 A | | 9/1999 | Katti et al. |
| 5,969,135 A | | 10/1999 | Ramasamy et al. |
| 5,990,479 A | | 11/1999 | Weiss |
| 6,114,038 A | * | 9/2000 | Castro et al. ......... 428/402.24 |
| 6,179,912 B1 | * | 1/2001 | Barbera-Guillem et al. .. 117/68 |
| 6,221,602 B1 | | 4/2001 | Barbera-Guillem et al. |
| 6,261,779 B1 | | 7/2001 | Barbera-Guillem et al. |
| 6,306,610 B1 | * | 10/2001 | Bawendi et al. ............. 435/7.1 |
| 6,306,736 B1 | * | 10/2001 | Alivisatos et al. ......... 438/497 |
| 6,319,426 B1 | * | 11/2001 | Bawendi et al. ...... 252/301.4 R |
| 6,326,144 B1 | * | 12/2001 | Bawendi et al. ............... 435/6 |
| 6,855,551 B2 | * | 2/2005 | Bawendi et al. ............... 436/6 |
| 2003/0059635 A1 | | 3/2003 | Naasani |

OTHER PUBLICATIONS

Norris et al., 1996, Physical Review B. 53:16338-16346.
Nirmal et al., 1996, Nature 383: 802-804.
Empedocles et al., 1996, Physical Review Letters 77: 3873-3876.
Murray et al., 1996, Science 270: 1355-1338.
Effros et al., 1996, Physical Review B. 54: 4843-4856.
Sacra et al., 1996, J. Chem. Phys. 103: 5236-5245.
Murakoshi et al., 1998, J. Colloid Interface Sci. 203: 225-228.
Optical Materials and Engineering News, 1995, vol. 5, No. 12.
Murray et al., 1993, J. Am. Chem. Soc. 115: 8706-8714.
Kho et al. 2000, Biochem. Biophys. Research Commun. 272: 29-35.
Hines and Guyot-Sionnest 1996, J. Phys. Chem. 100: 468 (abstract).
Dabbousi et al., 1997, J. Phys. Chem. 101: 9463.
Chan and Nie, 1998, Science 281: 2016-2018.
Bruchez, Jr. et., 1998, Science 281: 2013-2015.
Aldana et al., 2001, J. Am. Chem. Soc. 123: 8844-8850 (abstract).
Danek, et al., Chem. Mater., 8:173-179, 1996 (abstract).
Rodriguez-Viejo et al., Appl. Phys. Lett., 70: 2132-2134, 1997 (abstract).
Peng et al., J. Am. Chem. Soc., 119: 7019-7029, 1997 (abstract).
Pluckthum, Immunol. Rev., 130:152-188, 1992.
Singer, et al., J. Immunol. 150: 2844-2857, 1993.
Stankova, et al., J. Peptide Sci., 5:392-398, 1999.
Tsiavaliaris, et al., Synlett., 3: 391-393, 2001.
Hoffman, et al., Bioconjug Chem 12: 354-363, 2001 (abstract).
Trends in BioTech. 16:135-140, 1998.
Adair, Immunological Reviews, 130:5-40, 1992.

* cited by examiner

*Primary Examiner*—Leszek Kiliman
(74) *Attorney, Agent, or Firm*—Pepper Hamilton LLP

(57) ABSTRACT

The present invention provides for detection apparatus with functionalized fluorescent nanocrystal compositions and methods for making and using these compositions in biological detection applications, material separations, and in the production of biosensors. The compositions are fluorescent nanocrystals coated with at least one coating material comprising ligands with functional groups or moieties with conjugated electrons and moieties for imparting solubility to fluorescent nanocrystals in aqueous solutions. The coating material provides for functionalized fluorescent nanocrystal compositions which are water soluble, chemically stable, and emit light with a high quantum yield and/or luminescence efficiency when excited with light. The coating material may also have chemical compounds or ligands with moieties for bonding to target molecules and cells as well as moieties for cross-linking the coating.

33 Claims, 8 Drawing Sheets

Phase contrast | Fluorescence

HIGHLY LUMINESCENT FUNCTIONALIZED SEMICONDUCTOR NANOCRYSTALS FOR BIOLOGICAL AND PHYSICAL APPLICATIONS

CROSS REFERENCES AND RELATED APPLICATIONS

This application is a continuation in part of U.S. Utility patent application Ser. No. 10/245,082, filed Sep. 17, 2002 which claims priority from U.S. Provisional Application Ser. No. 60/379,208, filed May 9, 2002, and U.S. Provisional Application Ser. No. 60/322,982, filed Sep. 17, 2001, now U.S. patent application Ser. No. 10/245,082, the disclosures of which are incorporated herein by reference in their entirety; this application is also related to application serial number [not yet assigned] filed on the same date as this application, entitled "FUNCTIONALIZED FLUORESCENT NANOCRYSTAL COMPOSITIONS AND METHODS OF MAKING", Attorney Docket No. 126433.1201, the contents of which is herein incorporated by reference. The incorporation by reference of these documents is not admitted to be prior art with respect to the present invention by its mention in the Cross Reference.

GOVERNMENT INTEREST

This invention was made, in part, with government support under contract DAAD17-01-C-0024 with the United States Army Research Laboratory. The government has certain rights in this invention.

FIELD OF INVENTION

This invention relates to the utilization of highly luminescent, soluble and stable semiconductor nanocrystals in biological applications, detection of molecules and the production of biosensors.

BACKGROUND OF THE INVENTION

Fluorescence-based analysis has become a powerful tool in scientific research, clinical diagnostics and many industrial applications. However, while fluorescent organic molecules such as fluorescein and phycoerethrin are used frequently in fluorescence detection systems, there are disadvantages in using these molecules separately or in combination. For example, photobleaching (fading of intensity under light sources) is a major problem that hinders the accuracy of quantitative measurements using these molecules. In addition, each type of fluorescent molecules typically requires excitation with photons of a different wavelength as compared to that required for another type of fluorescent molecules due to the relatively narrow absorption spectrum of each. Moreover, even when a single light source is used to provide a single excitation wavelength, often there is overlapping or insufficient spectral spacing between the emissions of different fluorescent molecules to permit individual and quantitative detection.

Semiconductor nanocrystals are now being evaluated as a promising tool for nonisotopic detection to replace conventional fluorescent molecules. Since the spectral characteristics of nanocrystals are a function of the size, nanocrystals produced in a narrow size distribution can be excited to emit a discrete fluorescence peak of narrow bandwidth. In other words, the ability to control the spectral characteristics of nanocrystals (narrow bandwidth, discrete emission wavelengths, a single wavelength can excite an array of nanocrystals with different emissions) is the major attracting point in their use. Another advantage of the nanocrystals is their resistance toward photobleaching under intensive light sources.

Examples of semiconductor nanocrystals are known in the art to have a core selected from the group consisting of CdSe, CdS, CdTe (collectively referred to as "CdX") (see, e.g., Norris et al., 1996, Physical Review B. 53: 16338–16346; Nirmal et al., 1996, Nature 383: 802–804; Empedocles et al., 1996, Physical Review Letters 77: 3873–3876; Murray et al., 1996, Science 270: 1355–1338; Effros et al., 1996, Physical Review B. 54: 4843–4856; Sacra et al., 1996, J. Chem. Phys. 103: 5236–5245; Murakoshi et al., 1998, J. Colloid Interface Sci. 203: 225–228; Optical Materials and Engineering News, 1995, Vol. 5, No. 12; and Murray et al., 1993, J. Am. Chem. Soc. 115: 8706–8714; the disclosures of which are hereby incorporated by reference), and ZnS (Kho et al. 2000, Biochem. Biophys. Research Commun. 272: 29–35).

As known in the art, a manual batch method may be used to prepare semiconductor nanocrystals of relative monodispersity (e.g., the diameter of the core varying approximately 10% between quantum dots in the preparation), as has been described previously (Bawendi et al., 1993, J. Am. Chem. Soc. 115: 8706). Advances in nanocrystal core production and improvements in narrowing the particle size distribution, the controllability of particle size, and the reproducibility of production have been achieved by a continuous flow process (U.S. Pat. No. 6,179,912, the disclosure of which is herein incorporated by reference). Core semiconductor nanocrystals, however, exhibit low fluorescence intensity upon excitation, lack of water solubility, lack of surface functional groups for linking with target molecules, and additionally, susceptibility to dissociation and degradation in aqueous environments with high ionic strength. The low fluorescence intensity has been ascribed to the presence of surface energy states that act as traps which degrade the fluorescence properties of the core nanocrystal.

Efforts to improve the fluorescence intensity involve passivating (or capping) the outer surface of a core nanocrystal in order to reduce or eliminate the surface energy states. Inorganic materials with higher band gap energy have been used for passivation; i.e., core nanocrystals have been passivated with an inorganic coating ("shell") uniformly deposited on the surface of the core nanocrystals. The shell which is typically used to passivate CdX core nanocrystals is preferably comprised of YZ wherein Y is Cd or Zn, and Z is S, or Se, or Te. However, the above described passivated semiconductor nanocrystals have been reported to have a limited improvement in fluorescence intensity (with reference to quantum yield), and to have solubility in organic solvents only. Organic molecules, such as tri-n-octyl phosphine (TOP) and tri-n-octyl phosphine oxide (TOPO) have been also used for passivation (see Murray et al., 1993, J. Am. Chem. Soc. 115: 8706–8714, Hines and Guyot-Sionnest 1996, J. Phys. Chem. 100: 468-, Dabbousi et al., 1997, J. Phys. Chem. 101: 9463. However, these passivated semiconductor nanocrystals have been reported to have a limited improvement in fluorescence intensity (with reference to quantum yield), to be soluble only in organic solvents, and to be easily displaced by different solvents.

To make fluorescent nanocrystals useful in biological applications or detection systems utilizing an aqueous environment, it is desirable that the fluorescent nanocrystals used in the detection system are water-soluble. "Water-soluble" is used herein to mean sufficiently soluble or suspendable in an aqueous solution, such as in water or water-based solutions or buffer solutions, including those used in biological or molecular detection systems as known by those skilled in the art. Particles and surfaces may also be characterized by their ability to be wet by a fluid. The fluid may be water or a solution of water and other liquids like ethanol. One method to impart water-solubility to semiconductor nanocrystals (e.g., CdX core/YZ shell nanocrystals) is to exchange the overcoating layer of TOP or TOPO with a coating, or "capping compound", which will impart some water-solubility. For example, a mercaptocarboxylic acid may be used as a capping compound to exchange with the organic layer (see, e.g., U.S. Pat. No. 6,114,038, the disclosure of which is herein incorporated by reference; see also, Chan and Nie, 1998, Science 281: 2016–2018). The thiol group of monothiol capping compound bonds with the Cd-S or Zn-S bonds (depending on the composition of the nanocrystal), creating a coating which is to some extent not easily displaced in solution, and imparting some stability to the nanocrystals in suspension.

Another method to make the CdX core/YZ shell nanocrystals water-soluble is by the formation of a coating of silica around the semiconductor nanocrystals (Bruchez, Jr. et., 1998, Sciernce 281: 2013–2015; U.S. Pat. No. 5,990, 479) utilizing a mercapto-based linker to link the glass to the semiconductor nanocrystals. An extensively polymerized polysilane shell has been reported to impart water solubility to nanocrystalline materials, as well as allowing further chemical modifications of the silica surface.

Depending on the nature of the coating compound, coated semiconductor nanocrystals which have been reported as water-soluble may have limited stability in an aqueous solution, particularly when exposed to air (oxygen) and/or light. For example, oxygen and light can cause mercapto-based monothiols used in capping and passivation to become catalytically oxidized, thereby forming disulfides which destabilize the attachment of the coating and might even play a role in oxidizing the core semiconductor (see, e.g., Aldana et al., 2001, J. Am. Chem. Soc. 123: 8844–8850). Thus, oxidation may cause the capping layer to migrate away from the surface of the nanocrystals, thereby exposing the surface of the nanocrystals resulting in "destabilized nanocrystals" that eventually form nonsolubule aggregates with low fluorescence intensity. In addition, current means for passivating semiconductor nanocrystals are still rather inefficient in increasing the fluorescence intensity to a level desired for detection systems (e.g., in providing a significant increase in sensitivity in fluorescence-based detection systems as compared to currently available fluorescent dyes).

As is evident from current progress in the process of producing semiconductor nanocrystals, it is important to supply the nanocrystals with a stable, and protective capping layer to achieve the desired combinations of properties. In other words, the capping layer must be designed in such a way that it is able to impart to the semiconductor nanocrystals improvement in fluorescence efficiency (quantum yield); water solubility; stability in aqueous solutions; stability in media with high ionic strength; resistance to the exposure to hostile environment with light, oxygen and ions; and the ability to bind ligands, molecules, probes of various types, and solid supports. Additionally, there remains a need for a nonisotopic detection system which results in generation of a signal comprising fluorescence emission of high intensity; can result in signal amplification; is not limited as to the chemical nature of the target molecule to be detected (e.g., versus detection of nucleic acid molecules only); can be used to bind molecular probes of various types (affinity molecules, oligonucleotides, nucleobases, and the like); and can result in simultaneous detection of more than one type of target molecule by utilizing a class of nonisotopic molecules that may be excited with a single excitation light source and with resultant fluorescence emissions with discrete fluorescence peaks that can be spectrally distinguished from each other (e.g., using detection means for fluorescence that is standard in the art).

It is an object of the present invention to provide fluorescent nanocrystals which provides a combination of properties including a significant enhancement of fluorescence intensity, water solubility, physical and chemical stability, and functionalization.

SUMMARY OF THE INVENTION

The present invention provides for detection apparatus with functionalized fluorescent nanocrystal compositions and methods for making and using these compositions in biological detection applications, material separations, and in the production of biosensors. The compositions are fluorescent nanocrystals coated with at least one material. The coating material has chemical compounds or ligand with functional groups or moieties with conjugated electrons and moieties for imparting high luminescence efficiency and solubility to coated fluorescent nanocrystals in aqueous solutions. The coating material provides for functionalized fluorescent nanocrystal compositions which are water soluble, chemically stable, and emit light with a quantum yield of greater than 50% when excited with light. The coating material may also have chemical compounds or ligands with moieties for bonding to target molecules and cells as well as moieties for cross-linking the coating. In the presence of reagents suitable for reacting to form capping layers, the compounds in the coating may form a capping layer on the fluorescent nanocrystal with the coating compounds operably bonded to the capping layer.

The present invention provides for detection apparatus with functionalized fluorescent nanocrystal compositions and methods for making and using these compositions in biological detection applications, material separations, and in the production of biosensors. The functionalized fluorescent nanocrystals are coated with a material comprised of heteroaromatic compounds or ligands with functional groups or moieties for imparting solubility to coated fluorescent nanocrystals in aqueous solutions. The coating material provides for functionalized fluorescent nanocrystal compositions which are water soluble, chemically stable, and emit high efficiency light with a quantum yield of greater than 10% and preferably greater than 50% when excited with light. The coating material may also have chemical compounds or ligands like isocyanates, alkyl cyanoacrylates, or alkyl phosphines with moieties for bonding to target molecules and cells as well as moieties for cross-linking the coating. In the presence of suitable reagents, for example but not limited to $ZnSO_4$ and $Na_2S$, the compounds in the coating may form a capping layer on the fluorescent nanocrystal with the coating compounds operably bonded to the capping layer.

The present invention provides for an apparatus and methods of using the apparatus for detecting a target species. The apparatus may include functionalized fluorescent nanocrystal composition with a quantum yield of at least 10% and preferably greater than 50%, an excitation source for exciting the functionalized fluorescent composition and a detector for detecting the light emitted from the semiconductor composition. The functionalized fluorescent nanocrystal composition of the apparatus may be bonded to target molecules, molecular probes, and target molecules bonded to molecular probes; these compositions may further be dissolved in an aqueous fluid with a surface energy of greater than 50 dynes/cm. The excitation source for the apparatus exciting the functionalized fluorescent nanocrystal composition may be a suitable source of light or an excitation source which is a β-emitter. The intensity and wavelength of the light emitted by the excited functionalized fluorescent nanocrystals is measured by a detector. By including an optional source of polarized light the apparatus may be used for detecting the fluorescent polarization of a sample composition. The detector in this apparatus is provided with polarization filters for detecting the intensity of polarized light in the parallel and perpendicular planes with respect to the incident lights.

The present invention provides for an apparatus for detecting the intensity of the magnetic flux of the excited functionalized fluorescent nanocrystal. The apparatus may also include an external magnetic field for separating the magnetically induced functionalized fluorescent nanocrystals.

The functionalized nanocrystals described in this invention display an unexpected increase in fluorescence intensity as compared to other semiconductor nanocrystal formulations known in the art. Intra-unit energy transfer between the imidazoles and the core nanocrystals may be playing a major role in the fluorescence enhancement. Other mechanisms may account for such increase in fluorescence intensity imparted to these functionalized, fluorescent nanocrystals, may essentially include, but are not limited to, eliminating mid-band and intermediate states, passivation, charge dislocation, higher band energy condensation and resonance, modification of the bandgap of the shell semiconductor, or a combination thereof. The concept of passivation has been previously described herein. The passivating effect is due to the capping of surface Cd or Zn atoms or the like by imidazole complexation and to the capping of the counter atoms (Se or S or the like) by complexation with the alkyl phosphine-containing compounds. As to charge dislocation, imidazole and alkyl phosphine moieties present in the coating, may be susceptible to excitation by a sufficient light source. Such excitation may lead to charge transfer from the imidazole and/or alkyl phosphine moieties to the nanocrystal structure thereby resulting in an increase in fluorescence intensity, as compared to a fluorescence intensity without such internal charge transfer (internal charge transfer meaning a transfer of energy that substantially comprises a transfer within the structure of a coated nanocrystal of which the imidazole and/or alkyl phosphine are part of, as opposed to a transfer limited only to a transfer of energy between neighboring nanocrystals). As for energy condensation and fluorescence, it is anticipated that the integration of the π electrons in the imidazole and phosphine moieties with the excited electrons at the higher energy band of the core crystal is producing an energy condensation effect that yields higher level of electron-hole coupling followed by radiative relaxation. Chemical modifications of semiconductor surfaces with organic or inorganic molecules can shift the band edges of a semiconductor positive or negative (JECS 142, 2625, (1995)). Since strong surface capping and passivation of core semiconductor nanocrystals by higher band gap energy materials or organic passivators (e.g., TOPO) do not significantly enhance the fluorescence intensity of core semiconductor nanocrystals, it seems that energy condensation, energy transfer and eliminating intermediate and mid band exciton states are the major factors that underlie the fluorescence enhancement. The functionalized, fluorescent nanocrystals of the present invention are functionalized to be water-soluble and to contain one or more reactive functionalities to which a molecular probe may be operably bound. The overall structure of the functionalized, fluorescent nanocrystals of the present invention closely resembles the structure of a miniature light emitting diode (LED) where the coating materials used in this invention play the roles of hole-blocking layer and electron-transport layer.

Luminescence is the emission of light from any substance and occurs from electronically excited states. Luminescence is divided into two categories, fluorescence and phosphorescence, depending on the nature of the excited state. When the return of the excited electrons to the ground state is spin-allowed, the return is fast and this process is termed fluorescence (typically, a 10 nano second process). When the return of electrons to the ground states is spin forbidden it takes longer time (>100 ns), and the emitted light is termed phosphorescence. Luminescence efficiency means the amount of light (in candela units for example) that can be produced from a sample of nanocrystals using unlimited source of energy, for example beta emitter, light, recombination of injected charge carriers, or electrical current. The term quantum yield or efficiency in this case is different because it describes the ratio of energy recovery after applying certain amount of energy as photons, while, luminescence efficiency is different because it describes the full capacity of the nanocrystals (or a light source) apart from the amount of energy applied. In the practice of embodiments of the present invention either the Quantum yield the luminescence efficiency or both are increased by the coating material compositions of this invention.

In other embodiments of this invention, the ligands of functionalized fluorescent nanocrystal may increase the fluorescence efficiency (quantum yield) upon binding to the surface of the nanocrystal. In another embodiment of this invention, the ligands of the functionalized fluorescent nanocrystals may increase the fluorescence efficiency by one or more of the following mechanisms: internal energy transfer (antenna effect), energy condensation, elimination of intermediate and mid band exciton states, and surface passivation.

The above and other objects, features, and advantages of the present invention will be apparent in the following DETAILED DESCRIPTION of the invention when read in conjugation with accompanying drawings in which reference numerals denote the same or similar parts throughout the several illustrated views and embodiments.

DETAILED DISCRIPTION OF THE INVENTION

Figure 1A:
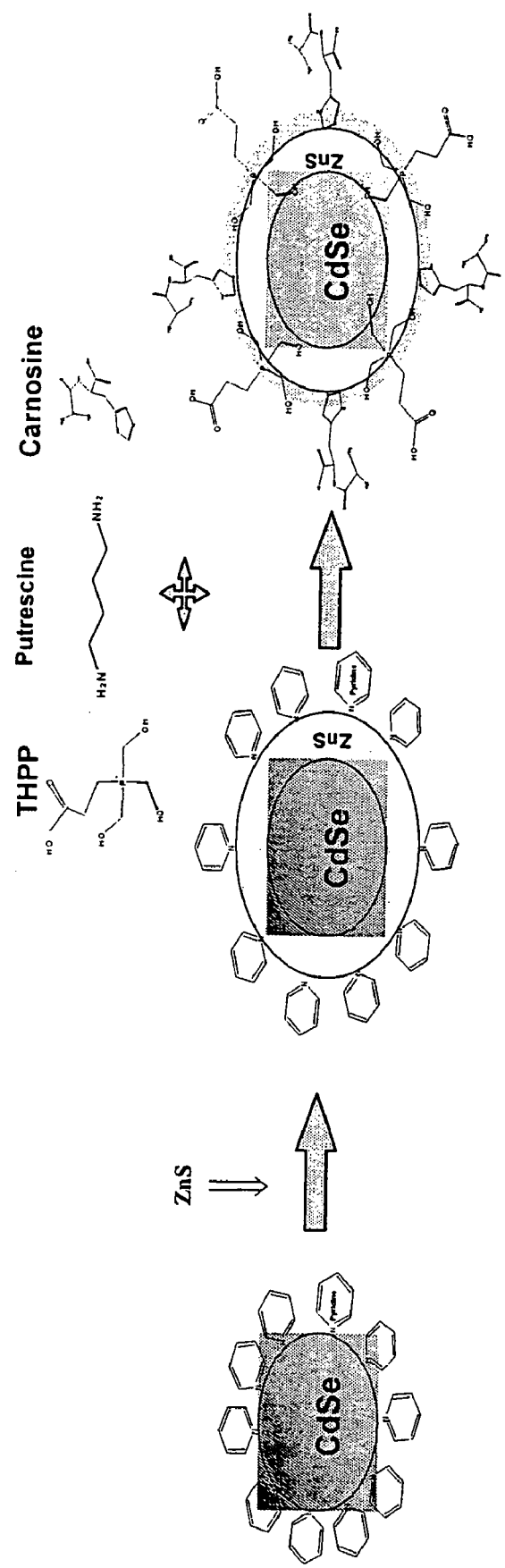
FIG. 1A is a schematic representation of the new coating system and a process for its formation.

Throughout the specification of the application, various terms are used such as "primary", "secondary", "first", "second", and the like. These terms are words of convenience in order to distinguish between different elements, and such terms are not intended to be limiting as to how the different elements may be utilized.

By the term "target molecule" is meant, for the purpose of the specification and claims to refer to a molecule of an organic or inorganic nature, the presence and/or quantity of which is being tested for; and which contains a molecular component (e.g., ligand or sequence or epitope or domain or portion or chemical group or reactive functionality or determinant, or the like) for which a molecular probe has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, a substrate, and the like. The target molecule may be in vivo, in vitro, in situ, or ex vivo.

By the term "molecular probe" is meant, for purposes of the specification and claims, to mean a molecule which has binding specificity and avidity for a molecular component of, or associated with, a target molecule. In general, molecular probes are known to those skilled in the art to include, but are not limited to, lectins or fragments (or derivatives) thereof which retain binding binding function, monoclonal antibodies ("mAb", including chimeric or genetically modified monoclonal antibodies which may be preferable for administration to humans). Peptides, aptamers, and nucleic acid molecules (including but not limited to, single stranded RNA or single-stranded DNA, or single-stranded nucleic acid hybrids, oligonucleotide analogs, backbone modified oligonucleotide analogs, morpholino-based polymers), and nucleobases. The term "nucleobase" is used herein to refer to a nucleic acid moiety including, but not limited to: nucleosides (including derivatives, or functional equivalents thereof, and synthetic or modified nucleosides, and particularly, a nucleoside comprising a reactive functionality (e.g., free amino group or carboxyl group)); nucleotides (including dNTPs, ddNTPs, derivatives or functional equivalents thereof, and particularly, a nucleotide comprising a reactive functionality (e.g., free amino group or carboxyl group); acyclonucleoside triphosphates (see, e.g., U.S. Pat. No. 5,558,991); 3'(2')-amino-modified nucleosides, 3'(2')-amino-modified nucleotides, 3'(2')-thiol-modified nucleosides, 3'(2') -thiol-modified nucleotides (see, e.g., U.S. Pat. No. 5,679,785); alkylamino-nucleotides (see, e.g., as a chain terminator, U.S. Pat. No. 5,151,507); nucleoside thiotriphosphates (see, e.g., U.S. Pat. No. 5,187,085); and the like. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')2, Fab', Fab, Fv, scFV, Fd' and Fd fragments. Methods for producing the various fragments or derivatives from mABs are well known in the art (see, e.g., Pluckthum, 1992, Immunol. Rev. 130:152–188; for example, via pepsin digestion, papain digestion, reduction of disulfide bridges, and methods described in U.S. Pat. No. 4,6142,334). Single chain antibodies can be produced as described in U.S. Pat. No. 4,946,778. The construction of chimeric antibodies is now a straightforward procedure (Adair, 1992, Immunological Reviews 130: 5–40) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, J Immunol. 150: 2844–2857). Methods for making a chimeric non-human/human mAb in general are described in detail in U.S. Pat. No. 5,736,137. Aptamers can be made using methods described in U.S. Pat. No. 5,789,157. Lectins and fragments thereof are commercially available. Oligonucleotide analogs, backbone modified oligonucleotide analogs, and morpholino-based polymers can be made using methods described in U.S. Pat. Nos. 5,969,135, and 5,596,086, U.S. Pat. Nos. 5,602,240, and 5,034,506, respectively. "Molecular probe" may also be used herein to refer to a plurality of molecules of molecular probe which may be operably bound to a functionalized, fluorescent nanocrystal.

By the terms "operably bind" and "operably bound" are meant, for purposes of the specification and claims to refer to fusion or bond or an association, of sufficient stability for the purposes of use in detection systems as described herein and standard conditions associated therewith as known in the art, formed between a combination of different molecules including, but not limited to, between a coating compound and fluorescents nanocrystal, between a coating material or compound and a molecular probe, between different molecular probes, and between molecular probe and target molecule or cell, or between a coating and a target molecule or cell. Operable bonding of the molecular probes and target molecules with the coating provides for complexes and functionalized fluorescent nanocrystal probes that may be used in compositions, detection apparatus, and detection methods of this invention. A coating may comprise one or more ligands. As known to those skilled in the art, and as will be more apparent by the following embodiments, there are several methods and compositions in which two or more molecules may be operably bound utilizing reactive functionalities. Reactive functionalities include, but are not limited to, bifunctional reagents (e.g., homobifunctional or heterobifunctional), biotin, avidin, free chemical groups (e.g., thiol, or carboxyl, hydroxyl, amino, amine, sulfo, and the like), and reactive chemical groups (reactive with free chemical groups). As known to those skilled in the art, the bond may compromise, but is not limited to, one or more of: covalent, ionic, hydrogen, van der waals, and the like.

Figure 1B:
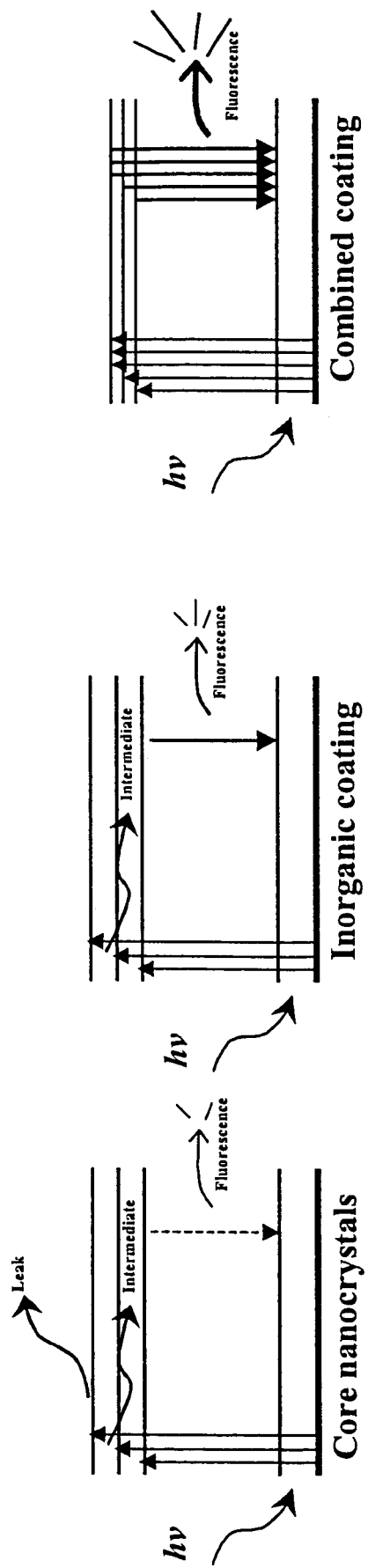
FIG. 1B is the anticipated energy change diagrams during the coating process according to the present invention.
Figure 1C:
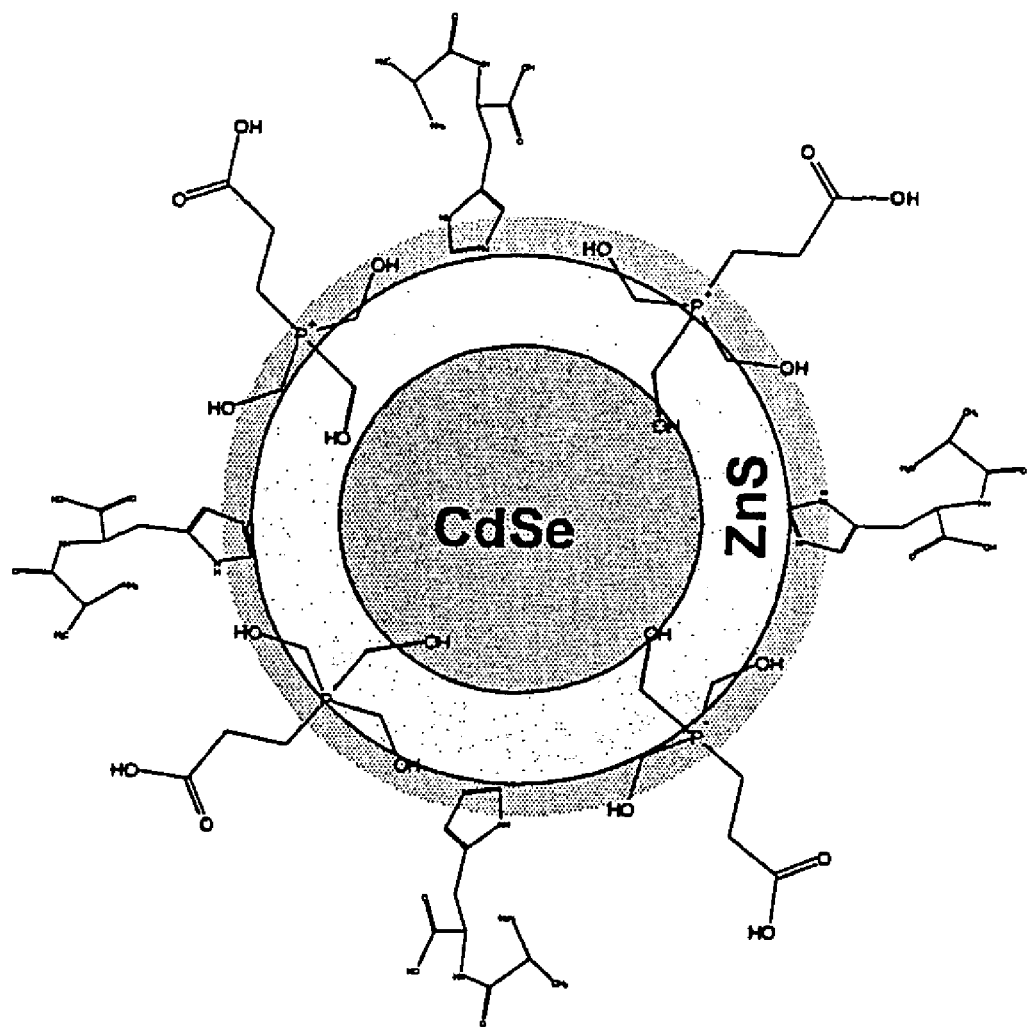
FIG. 1C is an illustration of the embodiment of the present invention.

By the term "imidazole-containing compound" is meant, for purposes of the specification and claims to refer to a heterocyclic or heteroaromatic molecule or ligand in a coating that has at least one imidazole group (e.g., imidazole ring) available for binding with the fluorescent nanocrystal or capping compound a metal such as zinc, cadmium, gallium, or other metal cation, or substrate containing such cation. In that respect, preferably at least one imidazole moiety is in a terminal position with respect to the structure of the molecule. The imidazole containing compound operably bonds to the fluorescent nanocrystal through the imidazole ring which comprises delocalized molecular orbitals. Generally, imidazole ring nitrogens serve as coordinating ligand, as illustrated in FIG. 1, to operably bind a metal ion such as zinc or cadmium. In a preferred embodiment, the imidazole-containing compound comprises additional reactive functionalities such as an amino acid, or two or more amino acids joined together (e.g., known in the art as "peptidyl" or "oligopeptide"), which may include, but are not limited to, histidine, carnosine, anserine, baleine, homocarnosine, histidylphenylalanine, cyclo-histidylphenylalanine, 5-amino-4-imidazolecarboxamide, histidylleucine, 2-mercaptoimidazole, boc-histidine hydrazide, histidinol, 1-methulhistidine, 3-methylhistidine, imidazolysine, imidazole-containing ornithine (e.g., 5-methylimidazolone), imidazole-containing alanine (e.g., (beta)-(2-imidazolyl)-L(alpha) alanine), carcinine, histamine, and the like. These histidine-based molecules or imidazole-containing amino acids may be synthesized using methods known in the art (see, e.g., Stankova et al., 1999, J. Peptide Sci. 5: 392–398, the disclosure of which is herein incorporated by reference in its entirety).

By the term "amino acid" is meant, as known in the art and for purposes of the specification and claims, to refer to a compound or ligand containing at least one amino group and at least one carboxyl group. As known in the art, an amino group may occur at the position adjacent to a carboxyl group, or may occur at any location, for example β and γ amino acids, along the amino acid molecule. In addition to at least one imidazole moiety, the amino acid may further comprise one or more additional reactive functionalities (e.g., amino, thiol, carboxyl, carboxamide, etc.). The amino acid may be a naturally occurring amino acid, a synthetic amino acid, a modified amino acid, an amino acid derivative, an amino acid precursor, in D (dextro) form, or in L (levo) form. Examples of derivatives may include, but are not limited to, an n-methylated derivative, amide, or ester, as known in the art. Consistent with the functionality of the amino acid, it acts as a coating for the fluorescent nanocrystals and may impart water-solubility, buffer sufficiently in a pH range between about pH 6 and about pH 10, functions as a coat which can increase fluorescence intensity, and has one or more reactive functionalities that may be used to operably bind at least one molecular probe. An amino acid of the aforementioned amino acids may be used in a preferred embodiment, and a preferred amino acid may be used separately in the composition of the present invention to the exclusion of amino acids other than the preferred amino acid. Carnosine (alanyl histidine) is a preferred imidazole-containing or histidine-based compound for coating the functionalized, fluorescent nanocrystals according to the present invention.

Other molecules or ligands may be used in place of imidazole in the practice of this invention. These ligands, (such as those disclosed in Cotton and Wilkinson, $3^{rd}$ Ed, Chapter 21) may operably bond to fluorescent nanocrystal surfaces, coordinate or chelate metal ions and preferably have Lewis base properties and or conjugated moieties. These molecules may also have moieties for imparting solubility or wettability in aqueous solutions to fluorescent nanocrystals coated with them. The molecules may also have chemical moieties for bonding to molecular probes, target molecules, and cells as well as moieties for cross-linking them. The ligand bonds to the fluorescent nanocrystal with its moiety that comprises delocalized molecular orbitals as illustrated in FIG. 1. In the presence of reagents suitable reagents like $ZnSO_4$ and $Na_2S$, these molecules or compounds may react to form a capping layer on the fluorescent nanocrystal with the molecules operably bonded to the capping layer. The molecules may also operably bond to atoms or ions on the surface of the nanocrystal. The result of using these molecules or compounds is a functionalized nanocrystal with enhanced luminescence, water solubility and chemical stability. These molecules or compounds have at least one Lewis acid and or a conjugated moiety in a terminal position with respect to the structure of the molecule. Generally, cyclic or linear unsaturated compounds with resonating electrons or with resonating heterogeneous rings frequently serve as coordinating ligand to operably bind a metal ion such as zinc or mercury, or cadmium. These molecules or compounds may comprise a heterogeneous ring, or two or more joined together, examples include, but are not limited to, thiazole, thiazole derivatives, oxazole, oxazole derivatives, pyrrole, pyrrole derivatives including doped or undoped poly-pyrrole oligomers, thiophene, thiophene derivatives including doped or undoped poly-thiophenes, furan, furan derivatives, pyridine, pyridine derivatives, pyrimidine, pyrimidine derivatives, pyrazine, pyrazine derivatives, triazine, triazine derivatives, triazole, triazole derivatives, phthalocyanine, phthalocyanine derivatives, porphyrin, porphyrin derivatives. These compounds may comprise unsaturated (olefin) hydrocarbons or their amine, phosphorus, oxygen derivatives, which may include but are not limited to acetylene, propyne, and allene. It is preferred that the molecule have suffucient p-electron density to engage in adduct formation or resonance on the surface of the semiconductor nanocrystal.

By the term "alkyl phosphine cross-linking compound" is meant, for purposes of the specification and claims to refer to a molecule or ligand that has at least one phosphine group available for binding or chelating a non metal such as Se, S or other non metals, or substrate containing such atoms, and has at least one functional group (e.g., hydroxyl, amino, thiol, carboxyl, carboxamide, etc) with ability to react with neighboring molecules. In that respect, preferably at least one phosphine moiety is in a terminal position with respect to the structure of the molecule as illustrated in FIG. 1. Generally, phosphine moieties frequently serve as coordinating ligand to operably bind with the fluorescent nanocrystal or capping compound a non metal or ion such as Se or S. In a preferred embodiment, the alkyl phosphine-containing compound comprises a phosphine group, or two or more phosphine groups joined together (e.g., in a polymeric form), which may include, but is not limited to, hydroxymethylphosphine compounds, and the like. Alkyl phosphine-containing compounds may be synthesized using methods known in the art (see, e.g., Tsiavaliaris et al., 2001, Synlett. 3: 391–393, Hoffman et al, 2001, Bioconjug Chem 12: 354–363, U.S. Pat. No. 5,948,386). As known in the art, an alkyl phosphine-containing compound may further comprise one or more additional reactive functionalities (e.g., hydroxyl, amino, thiol, carboxyl, carboxamide, etc.). Examples of derivatives may include, but are not limited to, a hydroxy methyl phosphine derivative, amide, or ester, as known in the art, and where consistent with the functions of the alkyl phosphine as a coating as described herein (e.g., imparts water-solubility, buffers sufficiently in a pH range between about pH 6 and about pH 10, functions as a coat and cross-linker which can increase stability and fluorescence intensity, and has one or more reactive functionalities that may be used to operably bind molecular probe). An alkyl phosphine of the aforementioned derivatives may be used in a preferred embodiment, and a preferred alkylphosphine may be used separately in the composition of the present invention to the exclusion of alkyl phosphines other than the preferred alkyl phosphine. Tris (hydroxy methyl) phosphine and beta-[Tris(hydroxymethyl)phosphino] propionic acid are particularly preferred alkyl phosphine-containing compound for coating, stabilizing and functionalizing fluorescent nanocrystals according to the present invention. Also known in the art is that cross-linked alkyl phosphine-containing compounds have additional ability to operably bind to metal atoms and/or ions such as zinc and cadmium. In this respect functionalized isocyanates or alkyl cyanoacrylates may also be useful for cross-linking and adduct formation with fluorescent nanocrystals in the practice of this invention.

By the term "fluorescent nanocrystals" is meant, for purposes of the specification and claims to refer to nanocrystals comprising semiconductor nanocrystals or doped metal oxide nanocrystals, to which may be operably bound various ligands including histidine-based or imidazole-containing compounds and phosphonium compounds. "Semiconductor nanocrystals" is meant, for purposes of the specification and claims to refer to quantum dots (also known as crystallite semiconductors) comprised of a core comprised of at least one of a Group II–VI semiconductor material (of which ZnS, HgS, and CdSe are illustrative examples), or a Group III–V semiconductor material (of which GaAs is an illustrative example), or a Group IV semiconductor nanocrystal, or a combination thereof. These core semiconductor nanocrystals may further comprise and be passivated with a "shell" or capping layer of material uniformly deposited on the core. The material may be comprised of an inorganic material with a higher band gap than the core nanocrystal. Inorganic materials typically used to passivate CdX (X=S, Se, Te) core nanocrystals are preferably comprised of YZ where "Y" is Cd, Hg, or Zn and "Z" is S, Se, or Te. Core CdX nanocrystals with a YZ shell can be made by the methods in: (see, e.g., Danek et al., 1996, Chem. Mater. 8: 173–179; Dabbousi et al., 1997, J. Phys. Chem. B 101: 9463; Rodriguez-Viejo et al., 1997, Appl. Phys. Lett. 70: 2132–2134; Peng et al., 1997, J. Am. Chem. Soc. 119: 7019–7029; 1996, Phys. Review B. 53: 16338–16346; the disclosures of which are hereby incorporated by reference). As known to those skilled in the art, the size of the core of the semiconductor nanocrystal correlates with the spectral range of emission. Table 1 is an illustrative example for CdSe.

TABLE 1

| Color | Size Range (nm) | Peak Emission Range |
|---|---|---|
| Blue | 2.1 to 2.9 | 536 to 500 |
| Green | 2.9 to 4.7 | 500 to 575 |

TABLE 1-continued

| Color | Size Range (nm) | Peak Emission Range |
|---|---|---|
| Yellow | 4.7 to 5.0 | 575 to 592 |
| Orange | 5.0 to 6.1 | 592 to 620 |
| Red | 6.1 to 10.2 | 620–650 |

In a preferred embodiment, the semiconductor nanocrystals are produced using a continuous flow process and system (see, U.S. Pat. No. 6,179,912), and may have a particle size that varies by less than +/−10% in the average particle size (as measured by diameter) in the range of approximately 1 nanometer (nm) to approximately 20 nm. Semiconductor nanocrystals useful in the practice of various embodiments of this invention may also be characterized in that the dimensions of the nanocrystals are comparable or smaller than their bulk exciton diameter so that they exhibit size dependent optoelectronic properties.

By the term "doped metal oxide nanocrystals" is meant, for purposes of the specification and claims to refer to nanocrystals comprised of: a metal oxide, and a dopant comprised of one or more rare earth elements. For example, metal oxides include, but are not limited to yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. Doped metal oxide nanocrystals with rare earth elements may include but are not limited to oxides of elements selected from the Lanthanide series such as europium (Eu), cerium (Ce), neodymium (Nd), samarium (Sm), terbium (Tb), gadolinium (Gd), holmium (Ho), thulium (Tm), and alloys containing these elememts. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth or rare earth metal combination in a doped metal oxide has a given color. By adjusting the nature of the dopant and or the concentration of the dopant, the doped metal oxide nanocrystals may emit (with a narrow emission peak) a color over an entire range of colors. For example, the emission color and brightness (e.g., intensity) of a doped metal oxide nanocrystal comprising $Y_2O_3$:Eu may depend on the concentration of the Eu dopant; e.g., emission color may shift from yellow to red with increasing Eu concentration. For purposes of illustration only, representative colors which may be provided by various dopants in $Y_2O_3$ are listed in Table 2

TABLE 2

| Fluorescent Color | Dopant |
|---|---|
| Blue | Thulium |
| Blue | Cerium |
| Yellow-green | Terbium |
| Green | Holmium |
| Green | Erbium |
| Red | Europium |
| Reddish | Samarium |
| Orange | Neodymium |
| Yellow | Dysprosium |
| White | Praseodymium |
| Orange-yellow | Europium + terbium |
| Orange-red | Europium + samarium |

Methods for making doped metal oxide nanocrystals are known to include, but are not limited to a sol-gel process (see, e.g., U.S. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection. Without enough dopant, the doped metal oxide nanocrystal would fail to emit sufficient detectable fluorescence, too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may be excited with a single excitation light source resulting in a detectable fluorescence emission of high quantum yield (e.g., a single nanocrystal having at a fluorescence intensity that may be a log or more greater than that a molecule of a conventional fluorescent dye) and with a discrete fluorescence peak. Typically, doped metal oxide nanocrystals have a substantially uniform size of less than 200 Angstroms, and preferably have a substantially uniform size in the range of sizes of from about 1 nm to about 5 nm. In one embodiment, the doped metal oxide nanocrystals are comprised of metal oxides doped with one or more rare earth elements, wherein the dopant comprising the rare earth element is capable of being excited (e.g., with ultraviolet light) to produce a narrow spectrum of fluorescence emission. In another embodiment, the doped metal oxide has both fluorescent properties (when excited with an excitation light source) and magnetic properties; thus, a polymeric microsphere (which is substantially nonmagnetic) embedded or labeled with a plurality of fluorescent nanocrystals (comprising doped metal oxide nanocrystals which are magnetic material) may form fluorescent microspheres which are magnetic.

By the term "functionalized fluorescent nanocrystals" is meant, for purposes of the specification and claims to refer to fluorescent nanocrystals which are coated. The coating may include but is not limited to cations, ligands, molecules with conjugated moieties as well as lyophilic and bonding moieties, cross linking molecules, and molecular probes. An example of such a coating material coating is an imidazole-containing compound and alkyl phosphine containing compound.

A functionalized fluorescent nanocrystal probe composition comprises a functionalized fluorescent nanocrystal emitting light with a quantum yield of 10% and preferably greater than 50% when irradiated with light and the functionalized fluorescent nanocrystal is operably bonded to a molecule. The molecule may comprise target molecules, cells, polynucleotides of known sequence, molecular probes or combinations of these. Preferably, the functionalized fluorescent nanocrystal is soluble in a fluid with a surface energy of greater than 50 dynes/cm.

Functionalized fluorescent nanocrystals according to the present invention are soluble in aqueous solutions and other fluids depending upon the ligands comprising the material coating. For example, they may be soluble in water, water and isopropyl alcohol mixtures or liquids with surface tensions below about 80 dynes/cm, and preferably in the range from about 30–73 dynes/cm. The solvent or solvent mixture used to solublize or suspend the functionalized nanocrystals may have a surface energy which is about the same as the surface energy of the particular coating material of the functionalized nanocrystal. The surface energy of coating will vary with the molecular properties and amount of the ligands in the coating material. The functionalized nanocrystals (FNC) of the present invention were soluble in water, mixtures of water and glycerol (50%), water and ethanol (10%), water and methanol (50%, ~35 dynes/cm), water and DMSO (50%), water and polyethylene glycol 200 (50%), and water and isopropyl alcohol (50%). The FNC were also soluble in 100% of glycerol, isopropyl alcohol particularly after adding other solvents to isopropyl alcohol. Functionalized fluorescent nanocrystals according to the present invention may operably bond molecular probes and target molecules, have increased fluorescence intensity when excited by a suitable excitation source (see, e.g., Example 1, 2, and FIGS. 2–5 herein); and may further demonstrate chemical stability in a pH range of from about pH 6.0 to about 10.5. Preferred functionalized, fluorescent nanocrystals in the apparatus and methods according to present invention, may be used to the exclusion of functionalized, fluorescent nanocrystals other than the preferred functionalized, fluorescent nanocrystals.

The overall combined coating of the core nanocrystal provides a unique interaction with the physical and energy processing properties of the core nanocrystal leading to high fluorescence water solubility. This is both functionally and fundamentally different than using zinc-histidine as nucleation centers for growing core nanocrystals (see, Kho et al., 2000, Biochem. Biophys. Res. Commun. 272: 29–35), and is both functionally and fundamentally different than using a layer of an overcoating semiconductor (e.g., ZnS) with a high band gap to improve the quantum confinement of the core nanocrystal (see, U.S. Pat. No. 6,322,901, U.S. Pat. No. 6,207,229, and U.S. Pat. No. 6,426,513). As an example, a preferred embodiment of the apparatus of this invention may include, a Group II–VI semiconductor core may be coated with a Group II–VI semiconductor shell (e.g., a ZnS or CdSe core may be coated with a shell comprised of YZ wherein Y is Cd or Zn, and Z is S, or Se) and an imidazole-containing compound cross-linked with an alkyl phosphine-containing compound. Preferably, the coating comprised of the semiconductor material (shell) and imidazole-containing compound as well as alkyl phosphine-containing compound both passivate the outer surface of the core nanocrystal onto which the coating is deposited. The functionalized fluorescent nanocrystal of this embodiment may be operably bonded to a target molecule and may provide increased fluorescent intensity in the apparatus of this invention.

In another preferred embodiment, a core nanocrystal (e.g., CdX core) produced using methods standard in the art is coated with a metal cation (preferably capable of forming a semiconductor material, preferably, with a high band gap energy) operably bound to an imidazole-containing compound cross-linked with an alkyl phosphine-containing compound, wherein the coat is uniformly deposited over the outer surface of the core/shell nanocrystal. The functionalized fluorescent nanocrystal of this embodiment may be operably bonded to a target molecule and may provide increased fluorescent intensity in the apparatus of this invention.

In another embodiment, a fluorescent nanocrystal may be coated with imidazole-containing compound cross-linked with alkyl phosphine-containing compound to produce the functionalized, fluorescent nanocrystals according to the present invention. The functionalized fluorescent nanocrystal composition may luminescence with an efficiency of greater than about 10-fold of that of non coated fluorescent nanocrystals when irradiated with light or other source of exitation. The functionalized fluorescent nanocrystal of this embodiment may be operably bonded to a target molecule and may provide increased fluorescent intensity in the apparatus of this invention.

In yet another embodiment, onto the outer surface of a core/shell nanocrystal is deposited a coating comprising imidazole-containing compound and alkyl phosphine-containing compound. The functionalized fluorescent nanocrystal of this embodiment may be operably bonded to a target molecule and may provide increased fluorescent intensity in the apparatus of this invention.

In another embodiment, the functionalized, fluorescent nanocrystals according to the present invention further comprises chemical or physical cross-linking of the coating comprising imidazole-containing compound and alkyl phosphine-containing compound to promote further stabilization of the coat of the functionalized, fluorescent nanocrystal. Chemical cross-linking can be achieved by using methods and reagents known in the art which may include, but are not limited to, formaldehyde, glutaraldehyde, acrolein, 1,6-hexane-bis-vinylsulfone, putrescine, alkyl diamines, and other organic triamines or polyamines. Physical cross-linking and/or curing can also be achieved by using methods known in the art which may include, but are not limited to, ultraviolet irradiation, microwave treatment, heat treatment, and radiation. The functionalized fluorescent nanocrystal of this embodiment may be operably bonded to a target molecule and may provide increased fluorescent intensity in the apparatus of this invention.

The present invention provides compositions comprising functionalized, fluorescent nanocrystals and or functionalized, fluorescent nanocrystal probes which can be used in a variety of types of fluorescence-based detection systems. Examples include, but are not limited to, building three dimensional dendrimers which function to generate and significantly amplify a detectable signal (thereby considerably improving the sensitivity of a non-isotopic detection system; see, e.g., U.S. Pat. No. 6,261,779, the disclosure of which is herein incorporated by reference). Another example is to use the functionalized fluorescent nanocrystals of the present invention to label nucleobases and provide fluorescence-labeled nucleobases for nucleic acid strand synthesis or nucleic acid sequence determination (see, e.g., U.S. Pat. No. 6,221,602, the disclosure of which is herein incorporated by reference). Another example is to use the functionalized fluorescent nanocrystals of the present invention to make fluorescent microspheres (e.g., beads) by either embedding microspheres with and/or to operably bind microspheres to functionalized fluorescent nanocrystals. Another example is to use the functionalized fluorescent nanocrystals of the present invention in fluorescent ink compositions suitable for printing on substrates. In this example, the functionalized fluorescent nanocrystal ink composition is applied to a substrate in an identifiable code pattern and is then excited with a suitable for purposes of identification, verification, security, or ornamentation.

Excitation sources suitable for characterizing the functionalized fluorescent nanocrystals of this invention include but are not limited to polychromatic ultraviolet and visible lamps, substantially monochromatic sources of light, polarized light, beta emitters including but not limited to $^{33}P$, $^{125}I$, and $^{3}H$. Sources of light may include low, medium, and high pressure lamps as well as lasers. Electric current and electron bombardment of the nanocrystals may also me used for excitation. Suitable detectors may include but are not limited to visual detection, photodiodes, photomultipliers, heat detectors and charge coupled device detectors (CCDs); detectors may also include the use of polarizing filters. The emission of light and its intensity from excited functionalized fluorescent nanocrystals may be measured in any direction with respect to the excitation source; preferably the emission intensity is measured parallel, perpendicular, or in both directions with respect to the excitation source.

As will be apparent to one skilled in the art, the functionalized, fluorescent nanocrystals according to the present invention may be used in a detection system that may include, but is not limited to, one or more of: an affinity assay (e.g., immunoassay such as an ELISA), fluorescent staining (e.g., immunofluorescent staining on a glass slide, fluorescent in situ hybridization, and the like), flow cytometry, cell imaging-based detection assays (e.g., cell-based ELISA or "cELISA", image cytometry, cells grown in standard high density microarrays), microarray-based detection assays (e.g., olignucleotide scanning arrays, combinational DNA arrays, microchips containing arrays of nucleic acid molecules or protein molecules, multi-channel microchip electrophoresis, and the like), microfluidics-based detection assays (e.g., "lab-on-a-chip" systems as known in the art), fluorescence-based biosensors (see, e.g., Trends in Biotech. 16: 135–140, 1999), nucleic acid sequencing, nucleic acid hybridization, nucleic acid synthesis or amplification, manufacturing of light emitting diodes, identification verification (e.g., identification card or bank card), fluorescent bead-based detection assays, molecular sorting (e.g., cell sorting by flow cytometry), and the like.

This example illustrates embodiments of a process of making the functionalized, fluorescent nanocrystals for the apparatus of the present invention. For this and subsequent examples, semiconductor nanocrystals comprising core nanocrystals were produced using a continuous flow process as described in the U.S. Pat. No. 6,179,912. The following parameters were used to produce nanocrystals of cadmium selenide (CdSe): 10 g TOPO; 18.9 ul of Me$_2$Cd (dimethyl cadmium; e.g., 2.63×10$^{-4}$ moles of Cd); 198.9 ul of TOPSe (1M solution of Se in TOP; e.g., 1.989×10$^{-4}$ moles of Se); 4.5 ml of TOP; nucleation temperature (Tn) of 300 C; growth temperature (Tg) of 280° C.; and flow rate of 0.1 ml/min. The resulting CdSe nanocrystals displayed fluorescence at a wavelength of 578 nm, with an excitation wavelength of 410 nm, and a narrow bandwidth at half height of about 29 nm.

The process of making functionalized, fluorescent nanocrystals may comprise contacting fluorescent nanocrystals, for example CdSe, Zn S or (CdSe)ZnS with a solution comprising a ligand or an imidazole-containing compound and then with a solution comprising alkyl phosphine-containing compound. When metal ions like Cd$^{+2}$ or Zn$^{+2}$ are present in solution or on the fluorescent nanocrystal, the ligand or the imidazole-containing compound operably binds to the metal cation and the alkyl phosphine-containing compound operably binds to the counterpart non metal element (e.g., S, Se, or the like) in producing a coat over the fluorescent nanocrystals in forming functionalized, fluorescent nanocrystals.

As previously described, the fluorescent nanocrystals which are coated by the process may comprise core semiconductor nanocrystals, core/shell semiconductor nanocrystals, doped metal oxide nanocrystals, or a combinations thereof. With respect to metal cations, imidazole-containing compounds have been reported to operably bind metal ions which may include, but are not limited to one or more of, Zn$^{2+}$, Cu$^{2+}$, Fe$^{2+}$, Ni$^{2+}$, Cd$^{2+}$, Hg$^{+2}$, Co$^{2+}$, and the like. With respect to non metal counter part anions, alkyl phosphine-containing compounds have been reported to operably bind to non metal elements which may include, but are not limited to one or more of, O, S, Se, Te, Po and the like.

For example, core fluorescent nanocrystals are prepared and firstly coated by an inorganic layer of ZnS according to methods known in the art to form core/shell type nanocrystals, and then the core/shell type nanocrystals are coated by a second coating solution comprising a ligand or an imidazole-containing compound and then with a solution comprising an alkyl phosphine-containing compound. The ligand or imidazole-containing compound operably binds to the metal cation if present (e.g., $Cd^{+2}$, $Zn^{+2}$ or the like) and the alkyl phosphine-containing compound operably binds to the counterpart non metal element (e.g., S, Se, or the like) in producing a coat over the fluorescent nanocrystals in forming functionalized, fluorescent nanocrystals. As a general guideline, the core/shell nanocrystals coating process may comprise inclusion of components comprising, per milligram of fluorescent nanocrystals: imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process.

For example a 30 mM carnosine (imidazole containing compound) solution in a 1 M CAPSO buffer (3-(Cyclohexylamino)-2-hydroxy-1-propanesulfonic acid, sodium salt, pH 9.6) was prepared. Other suitable buffers known in the art which provide buffering in a range of from about pH 8.0 to about pH 11, may be used in place of the CAPSO buffer (e.g., a sodium carbonate buffer, TAPS buffer (N-tris (hydroxymethyl) methyl-3-aminopropanesulfonic acid), and the like). To 10 ml of the carnosine solution was added 0.5 to 3 mg of CdSe nanocrystals (core crystals) suspended in a minimal volume (e.g., from about 60 ul to about 200 ul) of organic solvent (e.g., chloroform or pyridine). After mixing, and incubation for about 1 hr at room temperature, the organic phase was discarded. Then to the aqueous phase was added 1.2 ml of 60 mM THPP (beta-[Tris(hydroxymethyl) phosphino] propioninc acid, alkyl phosphine-containing cross-linker). The temperature of the reactions may be modified as would be known to those skilled in the art to affect the coating process. After one hour of gentle mixing, 100 ul of 1M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified. Suitable methods of purification include but are not limited to size exclusion chromatography, dialysis, centrifugation, and a combination thereof. For example the solution comprising functionalized, fluorescent nanocrystals was dialyzed against a suitable buffer such like PBS (phosphate buffered saline) using 3000 KD MCO dialysis membranes.

The process for making the functionalized, fluorescent nanocrystals was repeated, whereby the relative amounts of each component were varied. There are two measures of stability which may be used; the first, is decay in fluorescence intensity over time to a threshold of the initial value etc. Most stable crystals decay 1% in 24 hours, least stable decay 25% in 24 hours. The second measure of stability is the physical stability were there is no change in solubility, aggregation, cloudiness, or phase separation, stability toward repeated centrifugation and filtration, and toward dialysis and electrophoresis. From these formulation studies, a preferred ratio of components that showed optimal properties of fluorescence and stability (in an aqueous environment, and at a wide pH range) comprises: 1 to 2 mg of core/shell nanocrystals (e.g., CdSe/ZnS); 0.3 mmole carnosine; 0.15 mmole THPP; 0.15 mmole putrescine, and 1 mmole formaldehyde.

The process for making the functionalized, fluorescent nanocrystals was repeated and the relative amounts of each component were varied. The resultant functionalized, fluorescent nanocrystals were characterized by: stability in aqueous solutions in a pH range of about 6 to about 10, with optimal stability in the range of from about pH 7 to about pH 9; available reactive functionalities on the surface of the functionalized, fluorescent nanocrystals (in this case, carboxyl groups) to which molecular probe may be operably bound; and fluorescence intensity. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.35 mmole carnosine; 0.15 mmole THPP; 0.15 mmole putrescine, and 1 mmole formaldehyde.

Figure 2:
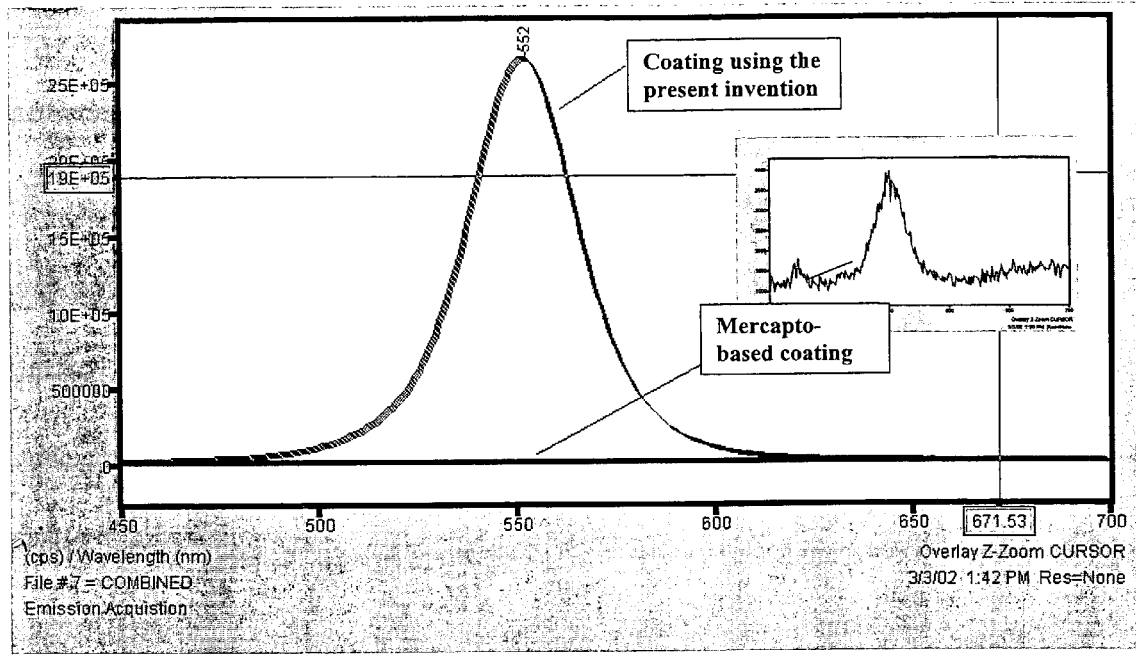
FIG. 2 is a graph showing a comparison of emission peaks of functionalized fluorescent nanocrystals using a mercapto-based method or the method of the present invention.
Figure 3:
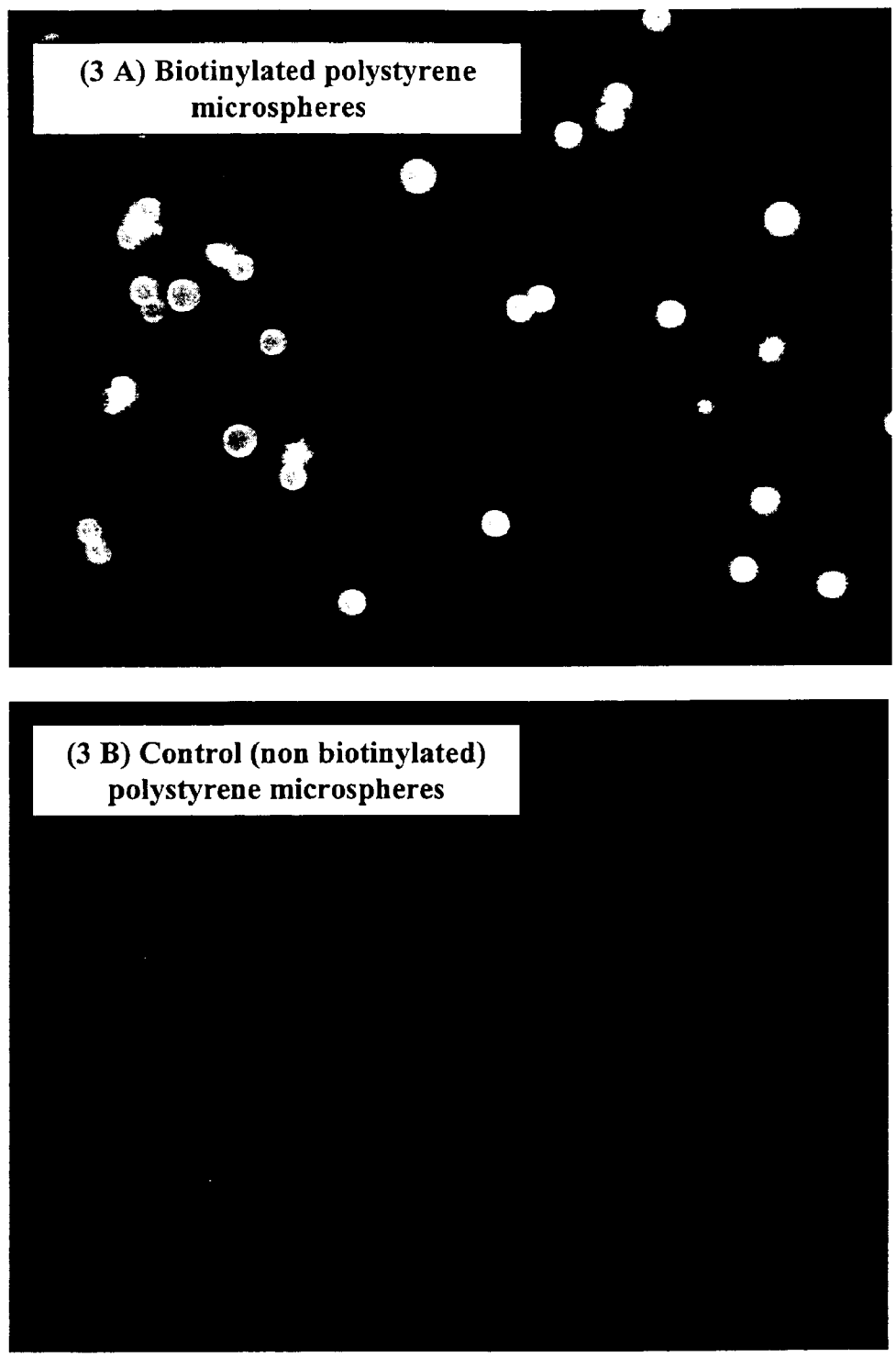
FIG. 3 is an image showing, after exposure to an excitation light source, biotinylated (A) and non biotinylated (B) polystyrene microspheres treated in parallel with covalently conjugated avidin to functionalized, fluorescent nanocrystals according to the method of the present invention.

These functionalized fluorescent nanocrystals showed unexpected enhancement of the characteristic fluorescence emission intensity comprising at least 50 fold to as much as about 1100 fold or more (see, e.g., FIG. 2 and inset of FIG. 2), when compared to the fluorescence intensity of functionalized fluorescent nanocrystals known in the art (e.g., CdX/YZ fluorescent nanocrystals in organic solvent or CdX/YZ fluorescent nanocrystals capped with mercapto-based compound) (see, e.g., FIG. 2). The comparison of characteristic fluorescence emission intensity was made with an equivalent amount of fluorescent nanocrystals made using core/shell nanocrystals from the same preparation; excitation with the same excitation light source (e.g., 410 nm); and detection using the same detection system.

In this example, provided is another embodiment of process of making functionalized, fluorescent nanocrystals by coating fluorescent nanocrystals with a coating comprising histidine as an imidazole-containing compound. As a general guideline, the core/shell nanocrystals coating process may comprise inclusion of components comprising, per milligram of fluorescent nanocrystals: imidazole-containing compound or ligand in an amount ranging from about 0.25 mmole to about 2.5 mmole; alkyl phosphine-containing cross-linker ligand in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process.

For example, prepared was a 30 mM histidine (imidazole containing compound) solution in a 1 M CAPSO buffer (3-(Cyclohexylamino)-2-hydroxy-1-propanesulfonic acid, sodium salt, pH 9.6). Other suitable buffers known in the art as previously described. To 10 ml of the carnosine solution was added 0.5 to 3 mg of CdSe nanocrystals (core crystals) suspended in a minimal volume (e.g., from about 60 ul to about 200 ul) of organic solvent (e.g., chloroform or pyridine). After mixing, and incubation for about 1 hr at room temperature the organic phase was discarded. Then to the mixture was added 1.2 ml of 60 mM THPP (beta-[Tris(hydroxymethyl) phosphino] propioninc acid, alkyl phosphine-containing cross-linker). After one hour of gentle mixing, 100 ul of 1M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified as previously described.

The process for making the functionalized, fluorescent nanocrystals was repeated, whereby the relative amounts of each component were varied. The resultant functionalized, fluorescent nanocrystals were characterized by: stability in aqueous solutions of the general pH range of about 6 to about 10, with optimal stability in the range of from about pH 7 to about pH 9; availability of reactive functionalities on the surface of the functionalized, fluorescent nanocrystals (in this case, carboxyl groups) to which molecular probe may be operably bound; and fluorescence intensity. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.35 mmole histidine; 0.15 mmole THPP; 0.15 mmole putrescine, and 1 mmole formaldehyde. The fluorescent emission from these functionalized fluorescent nanocrystal was 50 to 1100 fold greater when compared to the fluorescence intensity of functionalized fluorescent nanocrystals known in the art (e.g., CdX/YZ fluorescent nanocrystals in organic solvent or CdX/YZ fluorescent nanocrystals capped with mercapto-based compound). The comparison of fluorescence intensity was made as previously described.

In this example one or more molecular probes are operably bonded to the previously made functionalized fluorescent nanocrystals to form a functionalized fluorescent nanocrystal probe. An apparatus comprising these nanocrystals is used to detect the absence or presence of target molecules using the functionalized fluorescent nanocrystal with the molecular probe an excitation source and a detector. Such a composition may then be used in an assay to detect the presence or absence of a variety of target molecules for which the molecular probe has binding specificity. As will be apparent to one skilled in the art, the reactive functionalities on the functionalized, fluorescent nanocrystals which are available for use in operably binding molecular probe will depend on the chemical nature (or species) of the ligands, for example the imidazole and alkyl phosphine-containing compounds, comprising the coating on the functionalized fluorescent nanocrystals. For example, in using carnosine or other imidazole-containing amino acids (other than carnosine) and THPP or other alkyl phosphine-containing compounds as components of the coating, one or more reactive functionalities (e.g., free carboxyl group, amino group, and a combination thereof) may be used to operably bind to one or more reactive functionalities of a molecular probe.

A molecular probe having a free carboxyl-reactive group may be operably linked to molecule of an alkyl phosphine- or imidazole-containing compounds comprising the coating of a functionalized, fluorescent nanocrystal using methods known in the art (e.g., treatment with EDC (1-ethyl-3-[3-dimethyl-aminopropyl] carbdiimide), followed by treatment with sulfo-NHS (sulfo-N-hydroxysuccinimide)). Alternatively, a molecular probe having a free amino-reactive group (e.g., a carboxyl group) may be operably linked to a free amino group of a molecule of imidazole- or -alkyl phosphine-containing compounds comprising the coating of a functionalized, fluorescent nanocrystal using methods known in the art. If desirable, essentially the same procedure can be used to operably bond a molecule comprising a spacer arm between the imidazole- or alkyl phosphine-containing compounds on one side and the molecular probe on the other side of the space arm. Such spacers are well known in the art and are commercially available (see, e.g., product catalog of Pierce Co.).

To illustrate this aspect of the invention, the molecular probe avidin was operably linked using these reactions to the functionalized fluorescent nanocrystals previously prepared (Example 2) to form a complex. Procedures similar to these were also used to operably bond functionalized fluorescent nanocrystals to the following molecular probes: ConA, lectin, and IgG. The functionalized, fluorescent nanocrystals comprising a coating of THPP and carnosine (produced by the methods described in Example 2 herein), were operably bound to avidin. The amino groups of avidin were operably bound to the carboxyl groups of functionalized, fluorescent nanocrystals. Two milliliters of 100 ug/ml functionalized, fluorescent nanocrystals in MES buffer (MES 50 mM, NaCl 250 mM, pH6.5) were esterified by treatment with 5 mM EDC (1-ethyl-3-[3-dimethyl-aminopropyl] carbdiimide) and 10 mM sulfo-NHS (sulfo-N-hydroxysuccinimide). The resulting solution was mixed at room temperature for 15 minutes, and then was dialyzed against the MES buffer for 90 minutes using dialysis membrane with a molecular weight cut off (MWCO) of 3000 daltons. To the resulting solution was added 100 ug avidin (dissolved in 100 ul phosphate buffered saline (PBS)), and the entire solution was mixed at room temperature for 30 minutes. The reaction was terminated by adding 25 mM glycine and mixing for another 30 minutes. The solution was then purified from excess nanocrystals and reagents using ultrafiltration centrifugal membranes with a MWCO of 50KD.

A composition comprising functionalized, fluorescent nanocrystals operably bound to avidin was then evaluated using three different assays. First, the binding ability of a target molecule comprising biotinylated polystyrene microspheres (the beads being obtained commercially) for the functionalized fluorescent nanocrystals operably bound to avidin was evaluated. In this assay, 100 ul of a composition comprising functionalized, fluorescent nanocrystals operably bound to avidin was contacted with 50 ul of 1% suspension comprising biotinylated polystyrene microspheres for 15 minutes. The microspheres were then washed three times with buffer and centrifuged after each washing. The final volume was adjusted with PBS to 100 ul, and a drop was mounted on a glass slide. Examination of a preparation of biotinylated polystyrene microspheres, and of non biotinylated polystyrene microspheres (control) was performed under fluorescence microscope using 200× objective linked to a CCD camera as a detection system, and with an excitation source having light of wavelength of about 300 nm. As shown in FIG. 3A, fluorescence by the target molecules comprising the biotinylated polystyrene microspheres show that they were operably bound to the functionalized fluorescent nanocrystals with the avidin molecular probe; as shown in FIG. 3B, the non biotinylated microspheres did not fluoresce because they could not bond to the functionalized fluorescent nanocrystals with the avidin molecular probe.

Figure 4:
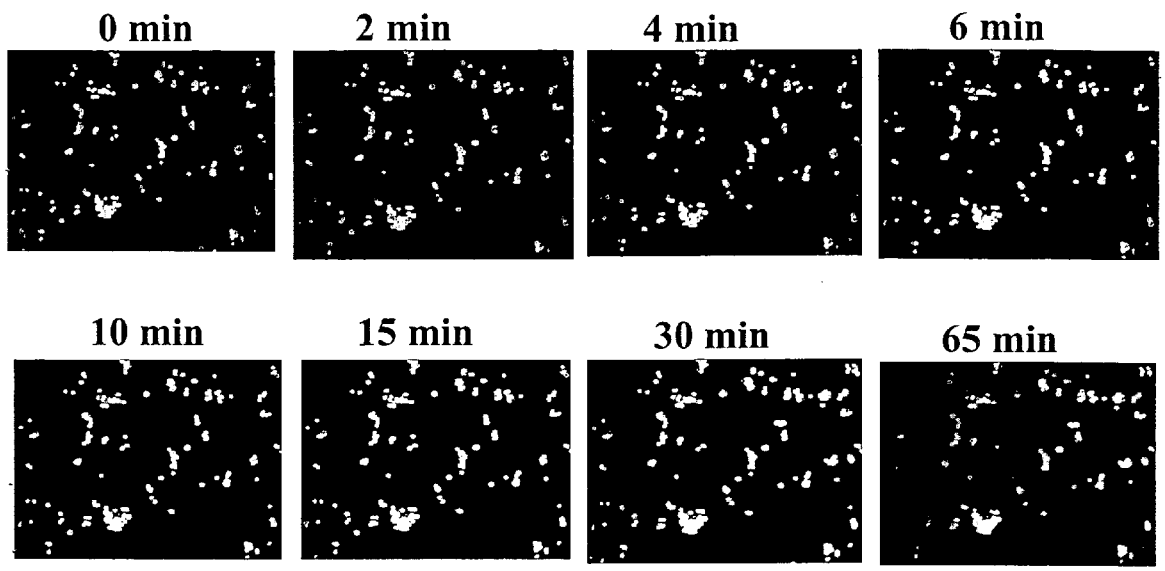
FIG. 4 is an image and a graph showing the photobleaching resistance of functionalized, fluorescent nanocrystals according to the method of the present invention when exposed to a direct UV light source of a fluorescence microscope.

In the second assay, the biotinylate microspheres were assayed for their resistance to photobleaching. Biotinylated microspheres stained with functionalized fluorescent nanocrystals operably bound to avidin were exposed to a direct UV light (excitation~300 nm) over a period from 0 to 65 minutes. As shown in FIG. 4 the staining of the biotinylated microspheres by functionalized, fluorescent nanocrystals operably bound to avidin was stable and did not photobleach over the period of exposure.

Figure 5:
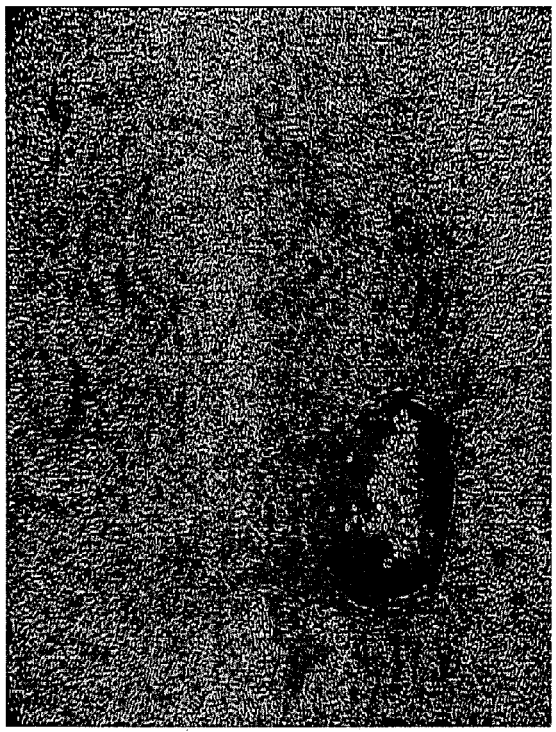
FIG. 5 An image of a liver microscopic section treated with primary biotinylated antibodies against mouse IgG and stained with avidinylated fluorescent nanocrystals functionalized according to the method of the present invention.
Figure 5:
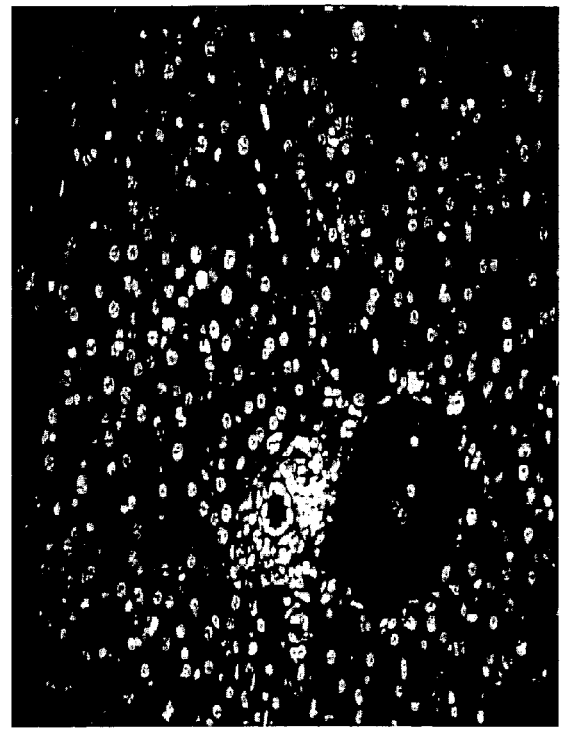
Figure 6:
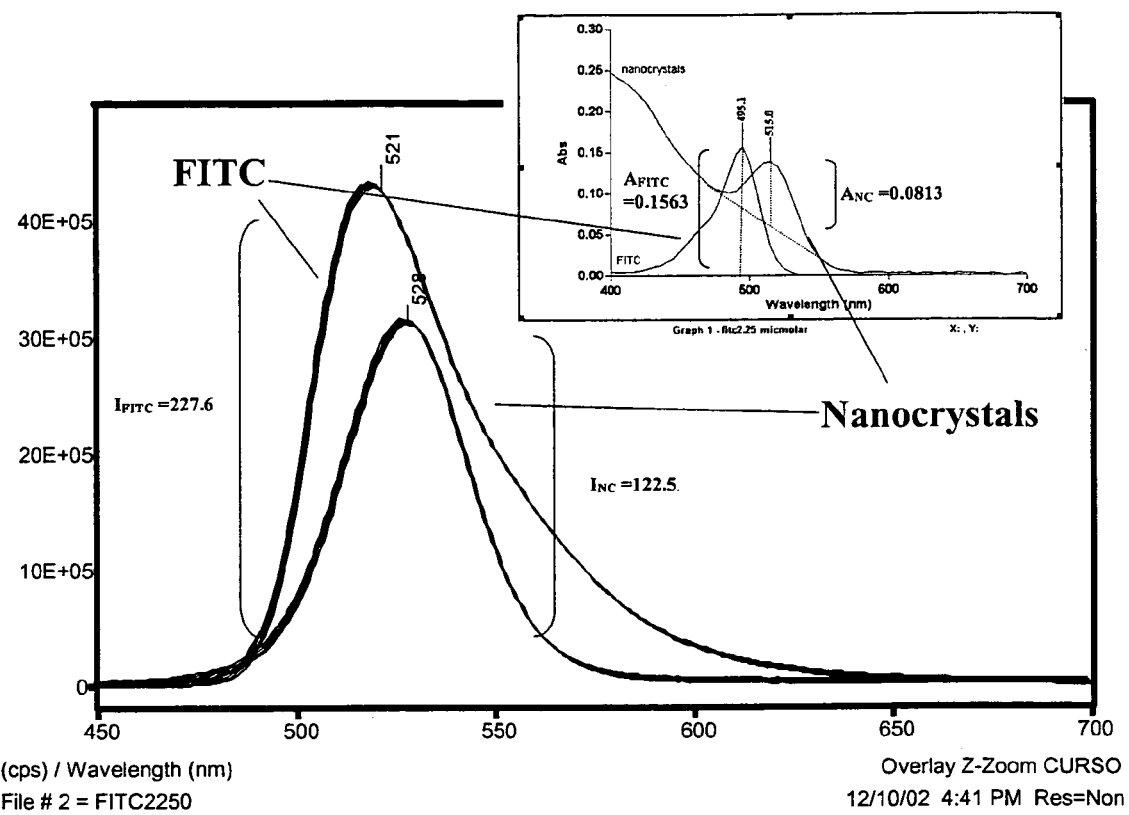
FIG. 6 A comparison of UV and fluorescence spectra and quantum yield for fluorescein isothiocyanate (FITC) and functionalized fluorescent nanocrystals of an embodiment of the present invention. Quantum yield (QY) value of the functionalized nanocrystals was determined relative to FITC (QY=0.75~0.95) in sodium borate buffer (50 mM, pH 9.0) using the equation: QYNC=QYFITC (INC/IFITC) (AFITC/ANC) (n/n')2, where, INC and IFITC are the integrated fluorescence intensity of nanocrystals and FITC, respectively; and ANC and AFITC are the UV absorbance maxima at excitation for nanocrystals and FITC respectively; and n and n' are the refractive indices of the solvents (sodium borate for both samples). According to the above equation the QYNC=0.73~1.

In the third assay, paraffin-embedded liver microscopic sections were treated with primary biotinylated antibodies against mouse IgG using methods well known in the art. These treated sections were then stained for about 90 minutes with a solution of functionalized fluorescent nanocrystals operably bound to avidin (5 ug/ml avidin conjugated nanocrystals in PBS). After a brief washing with PBS, the slides were examined under fluorescence microscope using 200× objective linked to a CCD camera as a detection system, and with excitation at about 300 nm. As shown in FIG. 5, the target molecules comprising biotinylated antibodies against mouse IgG were successfully operably bound to the composition comprising functionalized, fluorescent nanocrystals operably bound to avidin.

What is claimed is:

1. A functionalized fluorescent nanocrystal probe comprised of:
    a fluorescent nanocrystal;
    a coating material coating said fluorescent nanocrystal, said coating material being imidazole-based and further comprising a phosphine cross-linking compound; and
    a molecular probe material operably bound to said coating material.

2. The functionalized fluorescent nanocrystal probe of claim 1, wherein said fluorescent nanocrystal emits light with a quantum yield of greater than about 10%.

3. The functionalized fluorescent nanocrystal probe of claim 1, wherein said fluorescent nanocrystal emits light with a quantum yield of greater than about 30%.

4. The functionalized fluorescent nanocrystal probe of claim 1, wherein said fluorescent nanocrystal emits light with a quantum yield of greater than about 50%.

5. The functionalized fluorescent nanocrystal probe of claim 1, wherein said fluorescent nanocrystal emits light with a quantum yield of greater than about 70%.

6. The functionalized fluorescent nanocrystal probe of claim 1, wherein said coating material includes histidine.

7. The functionalized fluorescent nanocrystal probe of claim 1, wherein said coating material includes carnosine.

8. The functionalized fluorescent nanocrystal probe of claim 1, wherein the fluorescent nanocrystal is soluble in a fluid with a surface energy of greater than 35 dynes/cm.

9. The functionalized fluorescent nanocrystal probe of claim 1, wherein said fluorescent nanocrystals are soluble in an aqueous solution.

10. The functionalized fluorescent nanocrystal probe of claim 1, wherein said probe includes a polynucleotide of known sequence attached to said nanocrystal via a carboxy terminal portion of said polynucleotide.

11. The functionalized fluorescent nanocrystal probe of claim 1, wherein said fluorescent nanocrystal is cadmium selenide with a capping material including zinc sulfide that is operably bonded to cross linked histidine and (beta-(tris (hydroxymethyl)phosphino)propionic acid)).

12. The functionalized fluorescent nanocrystal probe of claim 1, wherein said fluorescent nanocrystal is cadmium selenide; and said coating material comprises zinc sulfide operably bonded to cross linked carnosine and (beta-(tris (hydroxyrnethyl)phosphino)propionic acid)).

13. The functionalized fluorescent nanocrystal probe of claim 1, wherein said molecular probe is chosen from the group consisting of avidin, ConA, lectin, and IgG.

14. The functionalized fluorescent nanocrystal probe of claim 13, wherein said molecular probe is avidin.

15. The functionalized fluorescent nanocrystal probe of claim 1, wherein said nanocrystal is a doped metal oxide nanocrystal.

16. The functionalized fluorescent nanocrystal probe of claim 1, wherein said doped metal oxide nanocrystal is magnetized when irradiated with light.

17. The functionalized fluorescent nanocrystal probe of claim 1, wherein said fluorescent nanocrystals have a characteristic spectral emission which is enhanced by the coating material.

18. The functionalized fluorescent nanocrystal probe of claim 1, wherein the fluorescent nanocrystal comprises a core material, a shell material, and a capping layer material.

19. The functionalized fluorescent nanocrystal probe of claim 18, wherein said core material is CdSe and said shell material is ZnS.

20. The functionalized fluorescent nanocrystal probe of claim 17, wherein said emission provides information about a biological state or event.

21. A method for detecting a target species, the method comprising: exciting a complex formed by operably bonding a fluorescent nanocrystal to a target molecule to form a complex wherein said fluorescent nanocrystal includes a imidazole-based coating material, wherein said coating material is further comprised of a phosphine cross-linking compound; and
    detecting the light emitted from said complex.

22. The method of claim 21, wherein the detecting further comprises detecting the intensity of light emitted from said complex perpendicular and parallel to an excitation source.

23. A method for separating materials comprising: introducing a doped metal oxide fluorescent core/shell nanocrystal soluble in fluids with a surface energy of at least 35 dynes/cm into a system; exciting said fluorescent nanocrystal to have a magnetic moment; and utilizing a magnetic field for separating the doped metal oxide fluorescent nanocrystals with the induced magnetic moment.

24. The method of claim 23, wherein said doped metal oxide fluorescent nanocrystals further comprise a molecule operably connected to said doped metal oxide fluorescent nanocrystal.

25. The method of claim 24, wherein said molecule is chosen from the group consisting of target molecules and molecular probes.

26. A coated nanocrystal comprising: a core comprising a first semiconductor material, a shell layer deposited on the core comprising a second semiconductor material, a coating material deposited on said shell layer comprised of an imidazole-based composition wherein said coated nanocrystal has a quantum yield of greater than 30% when excited with light.

27. The coated nanocrystal of claim 26, wherein the nanocrystal has a quantum yield of greater than 50% when excited with light.

28. The coated nanocrystal of claim 26, wherein the second semiconductor material is ZnS.

29. The coated nanocrystal of claim 26, wherein the second semiconductor material is ZnSe.

30. The coated nanocrystal of claim 26, wherein the first semiconductor material is selected from the group consisting of CdS, CdSe, CdTe, and mixtures thereof.

31. The coated nanocrystal of claim 30, wherein the second semiconductor material has a higher band gap than the first semiconductor.

32. The coated nanocrystal of claim 30, wherein the second semiconductor material is selected from the group consisting of ZnS, ZnSe, CdS, CdSe, and mixtures thereof.

33. The coated nanocrystal of claim 30, wherein the first semiconductor material is CdSe and the second semiconductor material is ZnS.

* * * * *

UNITED STATES PATENT AND TRADEMARK OFFICE
CERTIFICATE OF CORRECTION

| | | |
|---|---|---|
| PATENT NO. | : 7,214,428 B2 | Page 1 of 1 |
| APPLICATION NO. | : 10/410108 | |
| DATED | : May 8, 2007 | |
| INVENTOR(S) | : Imad Naasani | |

It is certified that error appears in the above-identified patent and that said Letters Patent is hereby corrected as shown below:

Column 22, line 5, please delete the word "hydroxyrnethyl" and substitute therefor:

--hydroxymethyl--

Signed and Sealed this

Twenty-sixth Day of June, 2007

JON W. DUDAS
*Director of the United States Patent and Trademark Office*